(12) United States Patent
Ahlers et al.

(10) Patent No.: US 8,226,970 B2
(45) Date of Patent: Jul. 24, 2012

(54) NON-WOVEN FIBER FABRIC (75) Inventors: Michael Ahlers, Eberbach (DE); Denis Reibel, Herrlisheim (FR); Jutta Hoffmann, Nussloch (DE)

(73) Assignee: Gelita AG, Eberbach (DE)

( * ) Notice: Subject to any disclaimer, the term of this patent is extended or adjusted under 35 U.S.C. 154(b) by 0 days.

(21) Appl. No.: 12/549,629

(22) Filed: Aug. 28, 2009

(65) Prior Publication Data
US 2010/0021517 A1 Jan. 28, 2010

Related U.S. Application Data (63) Continuation of application No. PCT/EP2008/001623, filed on Feb. 29, 2008.

(30) Foreign Application Priority Data

Mar. 2, 2007 (DE) .......................... 10 2007 011 606

(51) Int. Cl.
| A61K 9/70 | (2006.01) |
|---|---|
| A61K 9/00 | (2006.01) |
| A61K 38/36 | (2006.01) |
| A61P 7/04 | (2006.01) |
| D04H 5/00 | (2012.01) |
| D04H 3/00 | (2012.01) |
| B29C 47/00 | (2006.01) |

(52) U.S. Cl. ..................... 424/422; 424/443; 264/176.1; 442/344; 442/351; 514/1.1

(58) Field of Classification Search .................. None
See application file for complete search history.

(56) References Cited

U.S. PATENT DOCUMENTS

| 3,600,482 A | 8/1971 | Salyer et al. |
| 3,757,004 A | 9/1973 | Brown et al. |
| 5,733,994 A | 3/1998 | Koepff et al. |
| 6,596,296 B1 | 7/2003 | Nelson et al. |
| 2004/0110439 A1 | 6/2004 | Chaikof et al. |
| 2004/0266000 A1 | 12/2004 | Offermann et al. |

FOREIGN PATENT DOCUMENTS

| DE | 898 144 C | 11/1953 |
| DE | 199 26 083 | 12/2000 |
| DE | 102 06 517 | 9/2003 |
| DE | 10 2005 048 939 | 1/2007 |
| EP | 0 633 902 | 1/1995 |
| EP | 1 457 552 | 9/2004 |
| GB | 862428 | 3/1961 |
| JP | 3-97910 | 4/1991 |
| JP | 3086822 | 9/2000 |
| WO | WO 2006044881 A2 * | 4/2006 |
| WO | WO 2007/001405 | 1/2007 |
| WO | WO 2007/122232 | 11/2007 |

OTHER PUBLICATIONS

Kidoaki Biomaterials 26 (2005) 37-46.*
English translation of JP2005163204A.*
English translation of DE102005048939.*

* cited by examiner

Primary Examiner — David J Blanchard
Assistant Examiner — Garen Gotfredson
(74) Attorney, Agent, or Firm — Leydig, Voit & Mayer, Ltd.

(57) ABSTRACT

In order to provide a non-woven fiber fabric, in particular, in the form of a flat material or as part of a flat material which can be used as a biodegradable material in medicine, in particular, as an implant or carrier material for living cells (tissue engineering) but also a non-woven fiber fabric which can be used in food technology in a variety of applications, in particular, as a preliminary product for foods, a non-woven fiber fabric is provided containing fibers consisting of a gelatin material, wherein the thickness of the fibers is on average 1 to 500 μm and wherein the non-woven fiber fabric has a plurality of areas, at which two or more fibers merge into one another without any phase boundary.

17 Claims, 10 Drawing Sheets

NON-WOVEN FIBER FABRIC

CROSS-REFERENCE TO RELATED APPLICATIONS

This application is a continuation of international application number PCT/EP2008/001623 filed on Feb. 29, 2008, which claims the benefit of German application number 10 2007 011 606.5 of Mar. 2, 2007, which are each incorporated by reference in their entirety.

BACKGROUND OF THE INVENTION

The invention relates to a non-woven fiber fabric, also, in particular, in the form of a flat material or as part of a flat material, a method for its production as well as various uses of the non-woven fiber fabric.

The invention is aimed, in particular, at non-woven fiber fabrics which can be used as a biodegradable material in medicine, in particular, as implants or carrier materials for living cells (tissue engineering) but also at non-woven fiber fabrics which may be used in food technology in a variety of applications, in particular, as preliminary products for foods.

BRIEF SUMMARY OF THE INVENTION

For this purpose, a new non-woven fiber fabric is suggested in accordance with the invention which contains fibers which consist of a gelatin material and have a thickness of, on average, 1 to 500 µm, wherein the non-woven fiber fabric has a plurality of areas, at which two or more fibers merge into one another without any phase boundary. The special feature of the non-woven fiber fabrics according to the invention is to be seen, in particular, in the fact that the linking of the fibers in the non-woven fiber fabric can be attributed to the areas, at which two or more fibers form a point of connection, at which no phase boundaries are apparent and, therefore, material conditions which are universally the same can be observed at the points of connection.

These areas are not, therefore, formed by any adhesion or welding of fiber surfaces which are adjacent to one another but rather the special feature is to be seen in the fact that the fiber surfaces disappear when the point of connection is formed.

Particularly for the purposes of the application in medicine and, in this case, in particular, for the purposes of tissue engineering, average fiber thicknesses in the range of 3 to 200 µm, in particular, in the range of 5 to 100 µm are recommended. The preferred fiber thicknesses allow, in particular, a simple colonization of the non-woven fiber fabric with living cells for the formation of implants.

The non-woven fiber fabrics according to the invention may be easily produced with the open pore structure desired for the cell colonization and offer a very large, specific surface for this purpose.

At the same time, the non-woven fiber fabrics according to the invention form, when observed macroscopically, a carrier material which is beneficial for a homogenous cell distribution following the colonization. The interconnecting pore structure of the non-woven fiber fabrics according to the invention, which is superior to that of porous sponge structures, is particularly advantageous for the subsequent growth of cells.

The non-woven fiber fabrics according to the invention may also be achieved with a sufficient form stability which is also adequately maintained in the wetted state. This may be ensured, in particular, by an adequate number of individual fibers which have a large diameter.

The resorption of the carrier structure of the non-woven fiber fabric in the case of implants is also ensured on account of the biological tolerance of the gelatin material.

The gelatin material in the fibers is biodegradable in a simple manner and for controlling the degradation behavior of the fibers of the non-woven fiber fabric it is advantageously provided for the gelatin material of the fibers to be cross-linked at least partially. The degradation behavior may be controlled via the degree of cross-linking and also the strength of the non-woven fiber fabric influenced in a moist to completely wetted or swollen state.

In a particularly preferred embodiment of the present invention, the gelatin material of the fibers is predominantly amorphous. This has the advantage that a gelatin material of the fibers in the amorphous state can easily be wetted. This is particularly the case when the gelatin material of the fibers is present in an amorphous state to 60% by weight or more.

This may also be expressed as initial wettability with pure water which is intended to be 1 minute or less. This specification of time is measured in accordance with the time which is required for the absorption of a drop measuring 50 µl by a non-woven fiber fabric with the weight per unit area of 150 g/m$^2$. The good initial wettability is expressed, for example, by the fact that a sample of the non-woven fiber fabric placed on a surface of water will be wetted, as it were, instantaneously and by absorbing water will sink into the water.

The capillary suction effect may be used to characterize the structure of the non-woven fiber fabric, in particular, its cavity structure. In the case of preferred non-woven fiber fabrics with pure water, this should generate a height of rise of the water of 15 mm or more within 120 seconds.

In a further, preferred embodiment of the invention, the maximum water absorption capacity of the non-woven fiber fabric, which is brought about by or is co-dependent on, in particular, a swelling of the gelatin material used for the fibers, is at least four times the dry weight of the non-woven fiber fabric, i.e., preferably 4 g or more, in particular, 10 g or more per gram of non-woven fiber fabric.

Non-woven fiber fabrics according to the invention preferably have a surface energy of 25 mN/m or less, in particular, 10 mN/m or less. This facilitates the initial wetting of the non-woven fiber fabric.

The tear resistance, which is preferably 0.15 N/mm$^2$ or more at a specific weight per unit area of the non-woven fiber fabric in the range of 140 to 180 g/m$^2$ in the dry state, is of particular importance for the non-woven fiber fabrics according to the invention, wherein a breaking elongation in the hydrated state (state of maximum water absorption due to swelling) of the non-woven fiber fabric is, in addition, preferably 150%, in particular, 200% or more.

Such non-woven fiber fabrics are excellent to handle, in particular, in the case of medical applications in the dry state and also offer an adequate strength in the hydrated, i.e., swollen state and so they may be adapted very easily to the conditions of the body at the implant site when used as implant carrier materials. In particular, a satisfactory suturing strength is also achieved for fixing the implants.

Preferred non-woven fiber fabrics of the present invention have an open pore structure with a permeability of the non-woven fiber fabric to air of 0.5 l/min×cm$^2$ or more, wherein this parameter is determined in accordance with German Standard 9237. Non-woven fiber fabrics are particularly preferred, with which the gelatin material of the fibers is present in a partially cross-linked gel form, which means that the stability of the non-woven fiber fabric at the body temperature of a patient is sufficient, on account of the cross-linking, even in the swollen state, for it to be handled without the non-woven fiber fabric thereby tearing or being damaged in another way.

In this respect, those non-woven fiber fabrics are of importance, in particular, which form a closed-pore fibrous gel structure in a hydrated state. This means that the non-woven fiber fabrics, which can and should certainly have an open pore structure in the dry state, lose their open porosity on account of the considerable amounts of water absorbed by the gelatin parts and the swelling following therefrom and then form a closed-pore, fibrous gel structure. This is of particular significance when the tissue areas to be covered by an implant bleed profusely and the implant is also intended to be used at the same time as a cover for open wounds or for the purpose of stopping bleeding.

The non-woven fiber fabric of the present invention has, in particular, fibers consisting of gelatin material which are produced with a rotor spinning process and at least some of the fibers have an intertwined structure.

Preferred gelatin materials as starting materials for the production of fibers for the non-woven fiber fabric according to the invention have a gel strength of 200 Bloom or more.

Additional, preferred embodiments of the present invention relate to non-woven fiber fabrics of the type described above, with which the non-woven fiber fabric contains at least one additional type of fibers which are formed from an additional material different to the gelatin material.

Such additional materials, from which the additional type of fibers can be formed, are, in particular, chitosan, carrageenan, alginate, pectin, starch and starch derivatives, regenerated cellulose, oxidized cellulose and cellulose derivatives, such as, for example, carboxy methyl cellulose (CMC), hydroxy propyl methyl cellulose (HPMC), hydroxy ethyl cellulose (HEC) and methyl cellulose (MC). In addition, synthetic biocompatible polymers are suitable, such as, for example, polylactic acid and polylactate copolymers, polydihydroxysuccinic acid, polycaprolactons, polyhydroxybutanoic acid and polyethylene terephthalate. In addition, gelatin derivatives are suitable, such as, for example, gelatin terephthalate, gelatin carbamate, gelatin succinate, gelatin dodecyl succinate, gelatin acrylate (cf., for example, EP 0 633 902), as well as gelatin copolymers, such as, for example, gelatin polylactide conjugate (cf. DE 102 06 517).

The invention relates, in addition, to a flat material, containing a non-woven fiber fabric according to the invention which has already been explained in detail in the above. Such flat materials can contain one or several layers of the non-woven fiber fabric according to the invention.

The flat materials according to the invention contain a membrane extending parallel to the non-woven fiber fabric for certain application purposes.

The membrane can, in this respect, serve as a carrier layer for the non-woven fiber fabric and so very low weights per unit area can, in particular, be realized in the case of the non-woven fiber fabric.

Alternatively or in addition, the membrane can form a barrier layer which inhibits the proliferation of cells and so an undisturbed growth of the cells which are desired or have been introduced into the implant is possible, in particular, with the use as a carrier material for tissue engineering applications. In this connection, it is also advantageous when the membrane is permeable for cell nutrients.

The invention relates, in addition, to a flat material of the type described above, wherein the non-woven fiber fabric is colonized by living cells, in particular, chondrocytes or fibroblasts.

With these applications, fiber diameters of, in particular, on average 3 µm or more are used and so the cell colonization is simple to configure. In this respect, pore sizes of, on average, approximately 100 µm to approximately 200 µm are preferred.

The invention relates, in addition, to the use of the non-woven fiber fabric described above as well as the flat material likewise described above as a cell colonization material.

The invention relates, in addition, to the use of the non-woven fiber fabric described above as well as the flat material described above as a medical wound cover.

The invention relates, in addition, to the use of the non-woven fiber fabric described above as well as the flat material described above as a medical implant.

The invention relates, in addition, to the use of the non-woven fiber fabric described above as a food.

The non-woven fiber fabrics according to the invention and the flat materials according to the invention can also be used for the production of depot medicines. In this respect, it may also be provided for the gelatin material of the fibers to contain a pharmaceutical substance.

Optionally, in addition or alternatively, the non-woven fiber fabric according to the invention and the flat material according to the invention can serve as a carrier for a pharmaceutical substance.

A preferred pharmaceutical substance, in particular, for the use as a material for covering wounds is the substance thrombin.

In addition or alternatively, the pharmaceutical substance can contain cell growth factors, in particular, a peptide pharmaceutical, in particular, growth modulators, such as, for example, BMP-2, BMP-6, BMP-7, TGF-$\beta$, IGF, PDGF, FGF.

The invention relates, in addition, to a method for producing non-woven fiber fabrics of the type described above, wherein the method includes the steps of:

(a) providing an aqueous spinning solution which contains a gelatin material;
(b) heating the spinning solution to a spinning temperature; and
(c) processing the heated spinning solution in a spinning device with a spinning rotor;
(d) and, optionally, an additional treatment of the non-woven fiber fabric obtained by adding property-changing additions in a fluid or gaseous state of aggregation.

The method according to the invention operates as a rotation spinning method, with which the fibers or filaments generated by the spinning rotor are collected as non-woven fiber fabrics on a suitable collection device.

A suitable collection device is, for example, a cylinder wall which is arranged concentrically to the spinning rotor and which can, possibly, likewise be driven for rotation. A further possibility is the horizontal collection of the filaments on a base surface, for example, a perforated metal sheet which is arranged beneath the spinning rotor.

The flight time of the fibers or filaments can be predetermined via the distance between the exit openings of the spinning rotor and the collection device and this time is selected such that an adequate solidification of the spinning solution discharged in fiber form is made possible and so the fiber form is retained when impacting on the collection device.

This is aided, on the one hand, by the cooling of the fiber or filament materials during the flight time, on the other hand, by the gel formation of the gelatin and, in addition, by an evaporation of water or of the solvent.

The fibers or filaments generated by the spinning rotor may easily be collected in a state, in which points of connection between two or more fibers are formed in a plurality of areas of the non-woven fiber fabric and the fibers merge into one another at these points without any phase boundary.

In the optional additional treatment step (d), the non-woven fiber fabric according to the invention may be adapted to specific applications in a plurality of characteristics.

By cross-linking the gelatin material, the mechanical and, in particular, chemical properties can be modified. For example, the resorption properties for medical application purposes can be specified via the degree of cross-linking of the gelatin material.

The non-woven fiber fabric of the present invention, which is regularly highly flexible, may be stiffened in subsequent treatment steps, for example, in order to improve the form stability and to make the introduction into a target area easier.

The non-woven fiber fabrics according to the invention may be saturated and/or coated with liquid media in subsequent treatment steps. Other biodegradable polymer materials or also wax-like materials can, in particular, be considered for this purpose.

The non-woven fiber fabrics of the present invention, with which a fiber thickness of on average from 1 to 500 µm is generated, may be generated by means of the method according to the invention and described above, in particular, in a simple manner and wherein, in addition, the areas characteristic for the invention are formed, at which two or more fibers are connected or, as it were, melt into one another without any phase boundary. A spinning solution, with which the proportion of gelatin is in the range of approximately 10 to approximately 40% by weight, is preferably used for the method according to the invention.

The gel strength of the gelatin is, in this respect, preferably approximately 120 to approximately 300 Bloom.

The spinning solution is preferably heated to a spinning temperature in the range of approximately 40° C. or more, in particular, in the range of approximately 60 to approximately 97° C. These temperatures enable, in particular, a simple formation of the characteristic areas of the non-woven fiber fabrics, at which two or more fibers are connected to or merge into one another without any phase boundaries.

The spinning solution is preferably degassed prior to the processing in step (c) and so long fibers with a very homogeneous fiber thickness are obtained in the non-woven fiber fabric.

The degassing will preferably be carried out by means of ultrasound.

Preferably, a cross-linking agent will already be added to the spinning solution to generate partially cross-linked gelatin materials in the fibers. Cross-linking may, however, also be brought about and in addition in the case of the fibers already spun by bringing them into contact with a cross-linking agent, whether gaseous or in solution.

The method according to the invention can be carried out particularly reliably when the rotor is heated to a temperature of approximately 100 to approximately 140° C. This temperature is particularly suitable for processing the aqueous spinning solutions, which contain gelatin materials, in the rotation spinning method.

A further cross-linking will preferably be carried out on the non-woven fiber fabric which is already finished and this determines the final degree of cross-linking of the gelatin material in the non-woven fiber fabric and, therefore, its biodegradability.

Various methods are available for the cross-linking, wherein enzymatic methods, the use of complexing agents or chemical methods are preferred.

In the case of the chemical cross-linking, the cross-linking will be carried out by means of one or more reactants, in particular, with aldehydes, selected from formaldehyde and dialdehydes, isocyanates, diisocyanates, carbodiimides, alkyl dihalides and hydrophilic dioxiranes and trioxiranes, such as, for example, 1.4 butanediol diglycidether and glycerin triglycidether.

It is recommended, in particular, in the case of the medical application to remove surplus cross-linking agent from the non-woven fiber fabric or the flat material following the cross-linking.

As described above, it is preferable for a cross-linking agent to already be added to the spinning solution and for a further cross-linking to then be carried out on the finished non-woven fiber fabric, so-to-speak in a second step, until the desired degree of cross-linking is reached.

The non-woven fiber fabrics of the present invention can be produced, in particular, as extremely flexible flat materials, are thereby elastic and are very easy to shape. In addition, the non-woven fiber fabrics can be regarded as structures which are completely open in comparison with sponge structures which have likewise already been used as a carrier material for tissue engineering and are likewise porous but have cell walls.

In this respect, very small filament thicknesses may be produced, in particular, with the spinning rotor spinning method suggested in accordance with the invention, wherein the gelatin need be subjected to higher temperatures during the entire spinning process only for a very short time, i.e., the temperature burden on the gelatin material can be limited to a considerable extent with respect to time and leads to fibers consisting of a gelatin material which corresponds essentially to the initial gelatin material in its molecular weight spectrum.

Non-woven fiber fabrics according to the invention can have an essentially uniform average fiber thickness.

Alternatively, non-woven fiber fabrics can, within the scope of the present invention, have a proportion of fibers, the average fiber thickness of which differentiates them from the other fibers. They can, in particular, have a larger average fiber thickness. By using two or more fiber fractions in the non-woven fiber fabric which differ as a result of their average fiber thickness, its mechanical strength values can be influenced in a targeted manner.

Alternatively or in addition, two or more layers of non-woven fiber fabric can, on the other hand, be combined to form a flat material, wherein the individual layers can have fibers of different, average fiber thicknesses. It is, of course, also possible in the case of these flat materials to use layers of non-woven fiber fabric with fibers of an essentially uniform, average fiber thickness together with layers of non-woven fiber fabric with several fiber fractions having different, average fiber thicknesses.

Non-woven fiber fabrics with fiber fractions having different, average fiber thicknesses, e.g., approximately 7 µm together with approximately 25 µm may be realized with the method according to the invention in that a spinning rotor is used, in which spinning nozzles with nozzle openings of different sizes are provided during the spinning procedure.

When the non-woven fiber fabric according to the invention is used as a carrier material for living cells, the non-woven fiber fabric has a great advantage over sponge structures or woven fabric structures in that very varied cavities are offered for the storage of the cells and so the cells can find the storage locations which are ideal for them. This already applies for non-woven fiber fabrics which have a uniform, average fiber thickness.

These and further advantages of the present invention will be explained in greater detail in the following on the basis of the drawings as well as examples.

DETAILED DESCRIPTION OF THE INVENTION

Example 1

Production of a Non-Woven Fiber Fabric

A 20% aqueous solution of a pork rind gelatin (300 Bloom) is produced by mixing 20 g of gelatin and 80 ml of distilled water at room temperature. After the gelatin has swollen for a period of approximately 60 minutes, the solution is heated for one hour to 60° C. and subsequently degassed with ultrasound.

Figure 1:
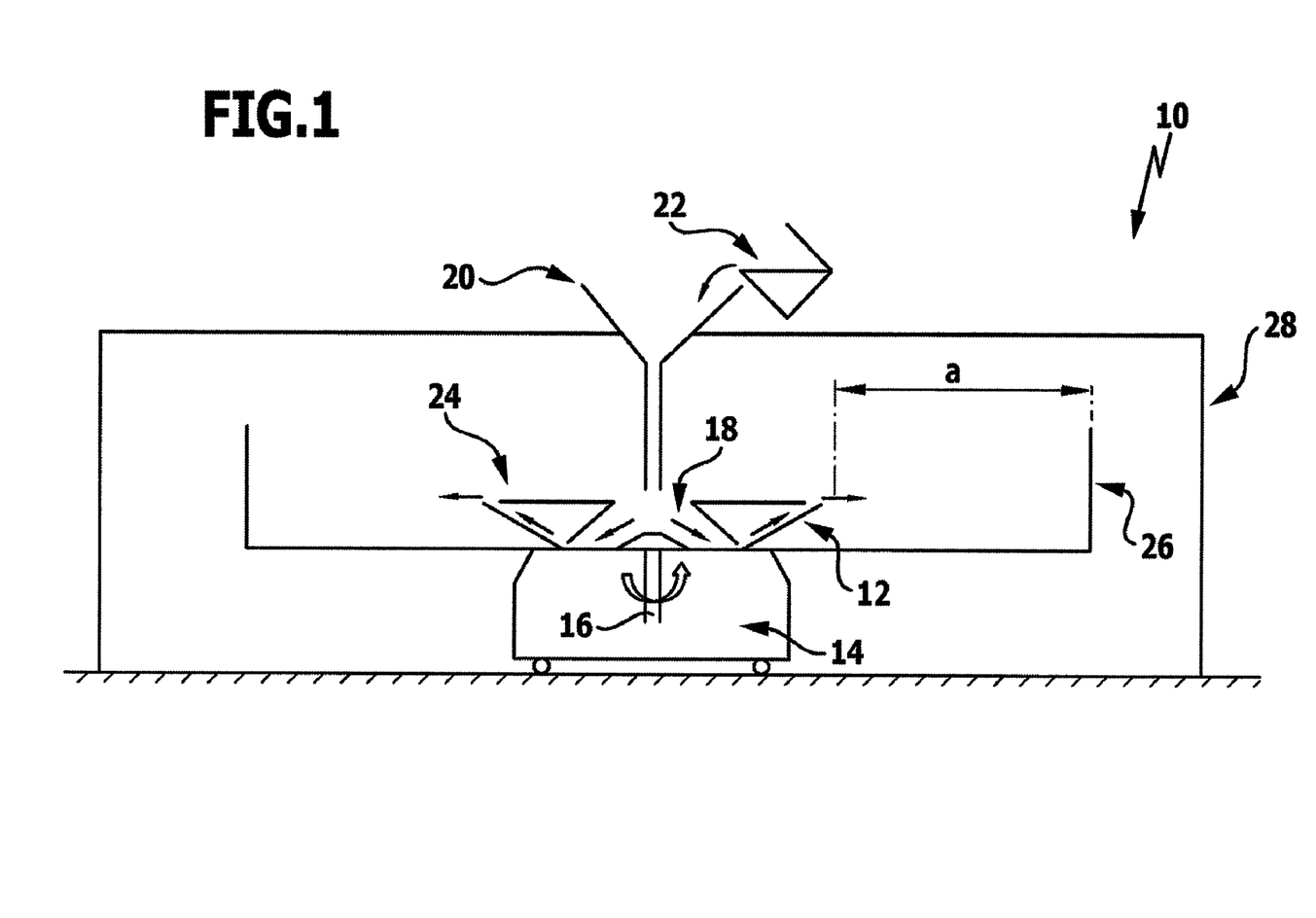
FIG. 1 shows a schematic illustration of a device for carrying out the method according to the invention.

This solution is then processed with a spinning device 10, as shown schematically in FIG. 1. Spinning devices of the type described in DE 10 2005 048 939 A1 are also suitable and reference is made to the content of this publication in full.

The spinning device 10 includes a spinning rotor 12 which can be caused to rotate about a vertical axis of rotation 16 by a drive unit 14.

The spinning rotor 12 has a container 18 for accommodating the aqueous gelatin spinning solution which can be supplied continuously during the spinning procedure from a supply channel 22 via a funnel 20.

The container 18 has at its outer circumference a plurality of openings 24, via which the spinning solution is discharged in a filament form due to centrifugal force.

A collection device 26 in the form of a cylinder wall is provided at a predetermined distance a from the openings 24 and collects the spinning solution shaped to form filaments or fibers. On account of the flight time predetermined via the distance a at a specific rotational speed of the spinning rotor 12, the spinning solution forming the filaments or fibers will be solidified to such an extent that the filament form is essentially retained when impinging on the collection device 26; on the other hand, the areas, in which two or more fibers or filaments melt, as it were, into one another and create points of connection, at which the phase boundaries of the fiber sections abutting on one another are removed (cf., in particular, FIG. 2b), can still be formed.

The spinning rotor 12 together with the drive unit 14 and the collection device 26 are arranged in a housing 28 which separates a spinning chamber from the surroundings.

In the present example, the spinning rotor 12 is driven at a rotational speed of 2,000 to 3,000 U/min. The rotor 12 is heated to a temperature of 130° C. The gelatin solution is heated to 95° C. and supplied to the rotor 12 so that a continuous generation of filaments can be carried out. The filaments are collected on the collection device 26 as fleece by means of suction. The distance a is approximately 20 cm and, therefore, defines a flight time of approximately 0.01 m/sec.

The average diameter of the filaments or fibers obtained may be influenced via the size of the openings 24 of the container 18 of the spinning rotor 12, the rotational speed of the spinning rotor 12 as well as the concentration of gelatin in the spinning solution. In the present example, the diameter of the openings 24 is approximately 0.9 mm.

In the example specified above, filaments with a filament thickness in the range of 2.5 to 14 µm (average fiber thickness 7.5 µm±2.6 µm) are obtained. An example of a non-woven fiber fabric which can be obtained with the method according to the invention is illustrated in FIGS. 2a to c in different enlargements.

Figure 2A:
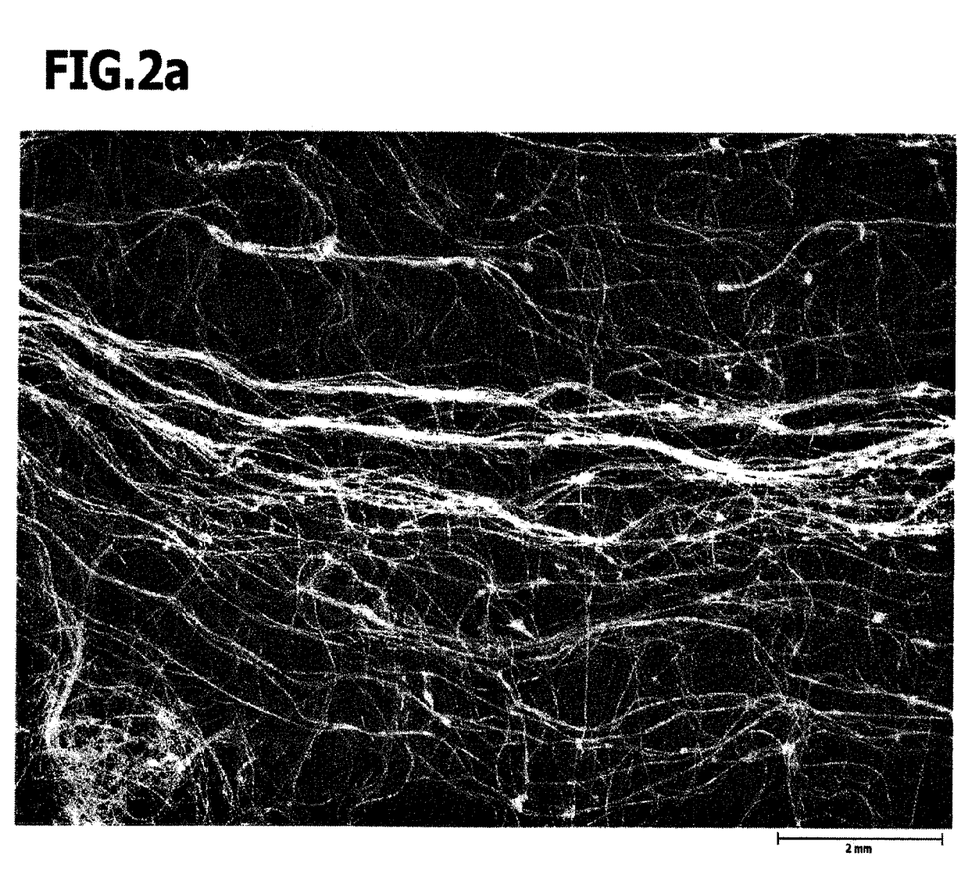
FIGS. 2a to c show micrographs of a non-woven fiber fabric according to the invention in different enlargements.

The relatively loose non-woven fiber fabric as shown in FIG. 2a can, of course, also be obtained with a higher filament or fiber density but non-woven fiber fabrics with the density as shown in FIG. 2a can also be connected, when several are placed one on top of the other, to form a self-supporting sheet material in the form of a fleece or, however, be placed on carrier materials, such as, for example, membranes or films.

Figure 2B:
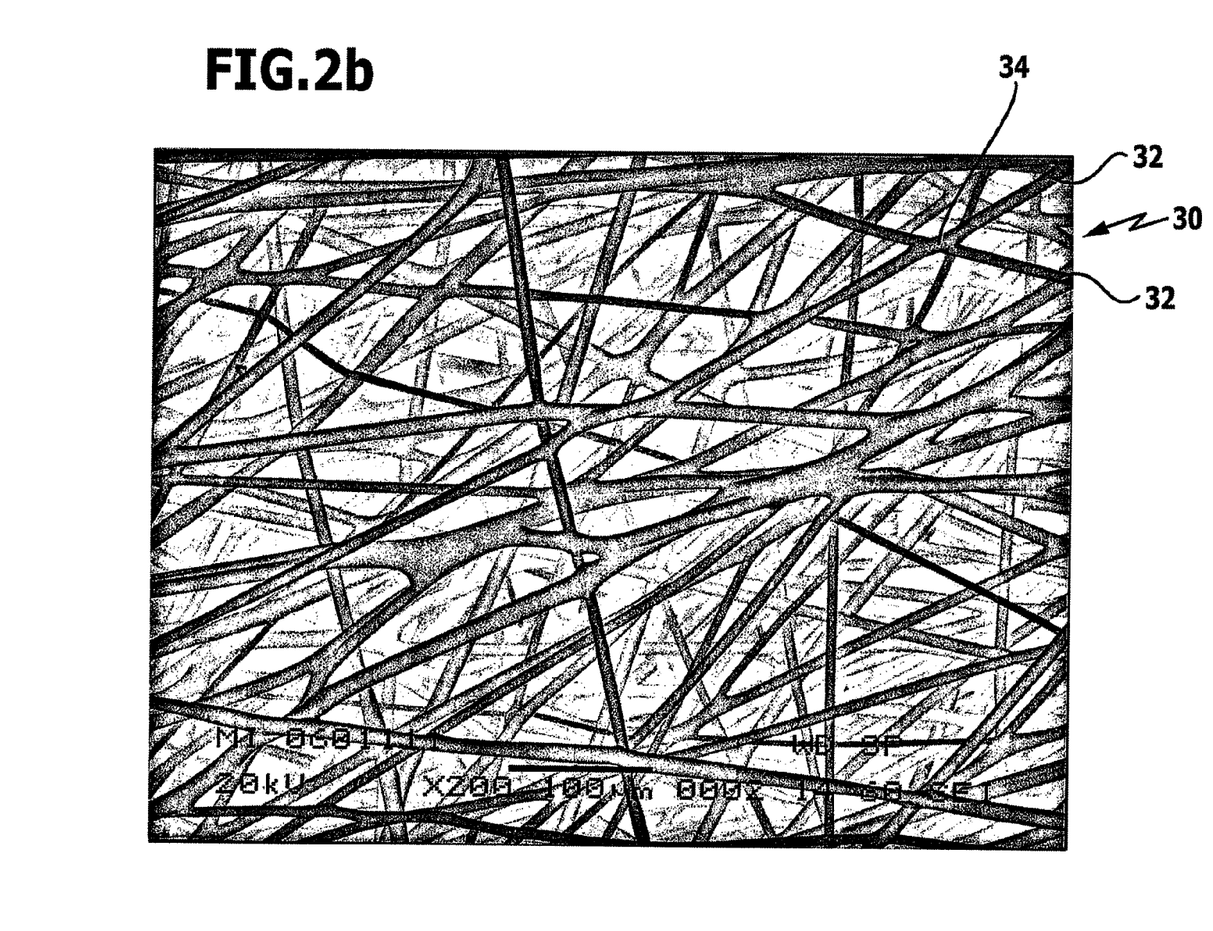

FIG. 2b shows, in a scanning electron micrograph, the non-woven fiber fabric 30 according to the invention which can be obtained with the method according to the invention with a plurality of fibers 32 consisting of a gelatin material and, in particular, the areas 34 which distinguish the invention and in which two or more fibers 32 are connected to one another without a phase boundary.

Figure 2C:
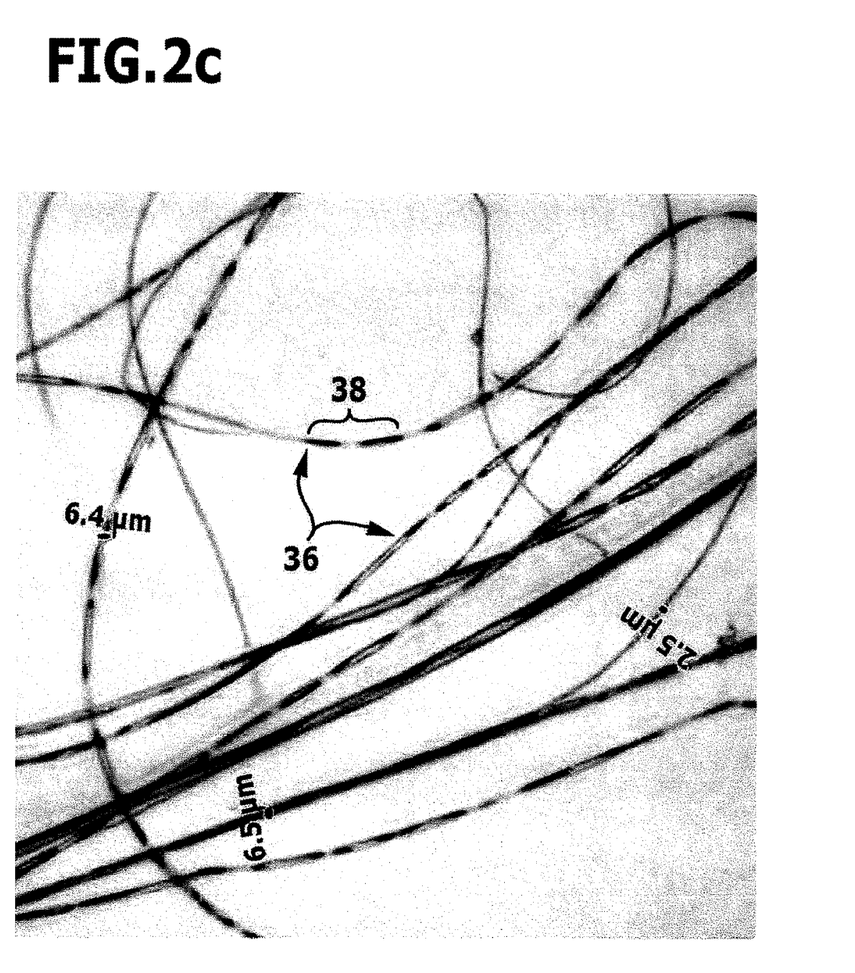

In FIG. 2c, the effect of the intertwining of the individual filaments 36 is made visible in a light micrograph in polarized light, wherein the intertwining sections are visualized by way of light-dark areas 38.

Example 2

Production of a Cell Carrier Material

Predetermined pieces of material are punched from the non-woven fiber fabric obtained in Example 1 and placed in layers on top of one another until a fleece with a desired weight per unit area, for example, in the range of approximately 20 to approximately 500 g/m² is achieved.

In the present Example, a multi-layered fleece, formed with a weight per unit area of 150 g/m2, is produced and, subsequently, partially cross-linked with the aid of gaseous formaldehyde. The cross-linking conditions in detail were as follows:

The non-woven fiber fabric is incubated in a gas atmosphere for approximately 17 hours over a formaldehyde solution of 10% by weight. Subsequently, the non-woven fiber fabric is slow cooled in a refrigerator for 48 hours at approximately 50° C. and 70% relative humidity. The cross-linking reaction is hereby completed and the surplus amount of formaldehyde (cross-linking agent) which was not used will be removed.

Samples were punched from fleeces produced in this manner and compared in their water absorption properties as well as mechanical properties with conventional cell carrier materials in the form of porous gelatin sponges as well as a material consisting of oxidized cellulose.

The width of the sample was 1 cm each time.

Figure 3:
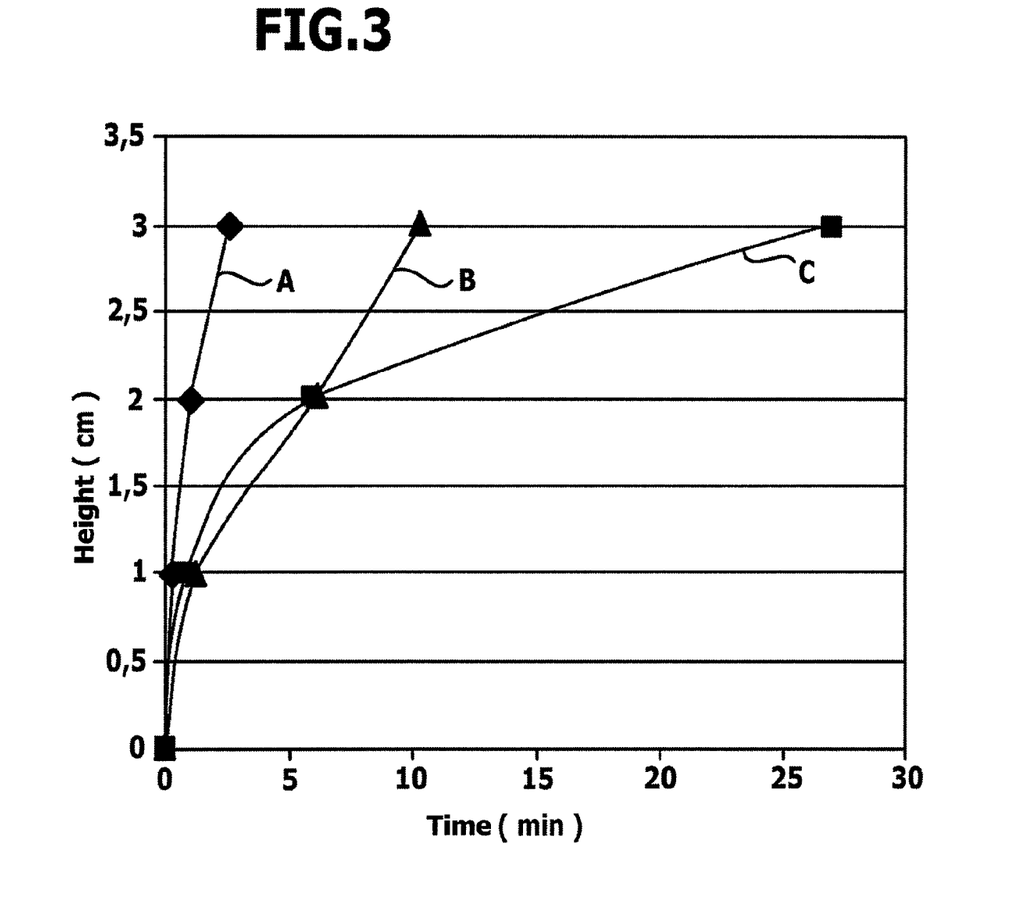
FIG. 3 shows a graph of height of rise/time for different materials.

FIG. 3 shows the height of rise of pure water plotted against the time for these three materials, wherein the curve designated with the letter A corresponds to the fleece according to the invention as a multi-layered non-woven fiber fabric, the curve B a conventional gelatin sponge and the curve C the conventional cellulose material which is commercially obtainable.

It is obvious from the comparison of the absorption of water over the unit of time that gelatin materials are clearly superior to the cellulose materials such as those used in sample C.

The sample of fleece from the non-woven fiber fabric according to the invention and according to curve A is, again, clearly superior to the gelatin material in a sponge form (curve B) in its water absorption capacity per unit of time, as is apparent from FIG. 3.

The practical advantage of this speed of water absorption, which is increased considerably, is to be seen in the fact that liquids, such as, for example, blood, can be absorbed more quickly and to a greater extent and, in the case of wounds which are to be treated, this leads to an improved staunching of the bleeding.

Figure 4A:
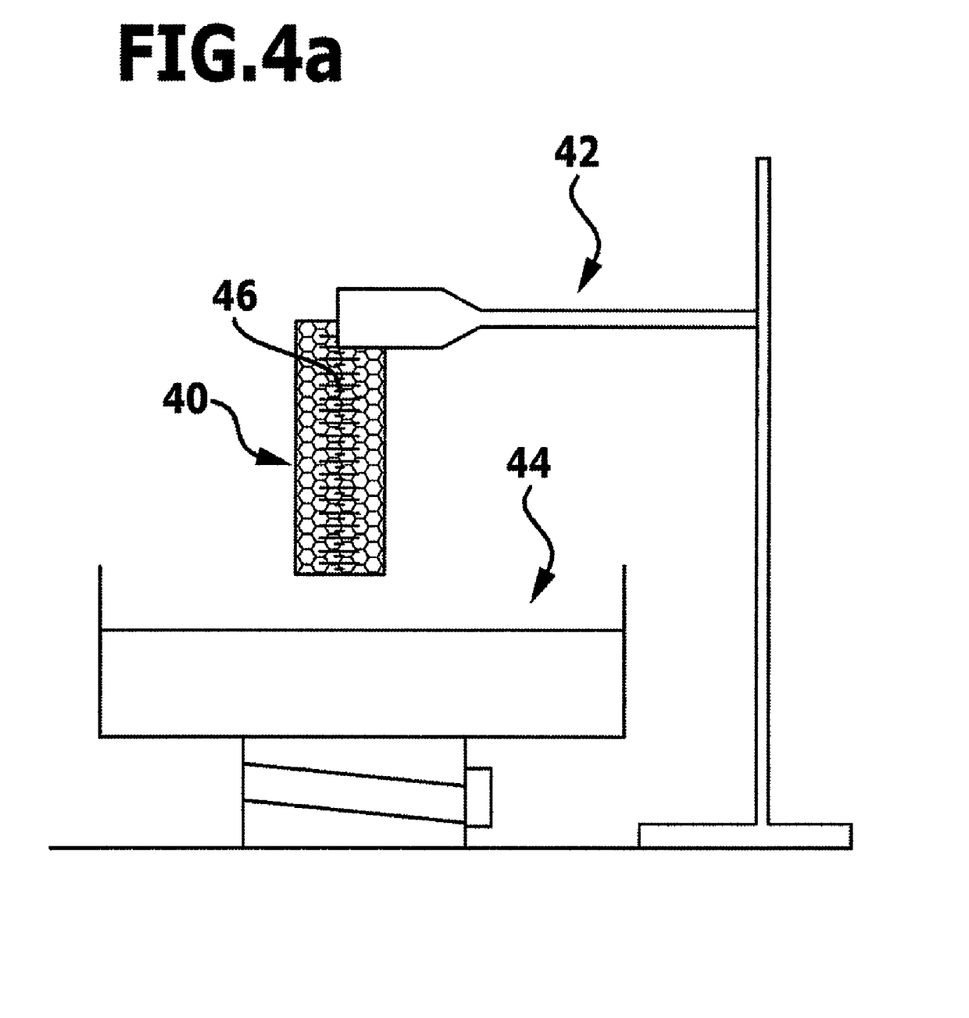
FIGS. 4a to c show a schematic illustration of a device for calculating the heights of rise illustrated in FIG. 3.
Figure 4B:
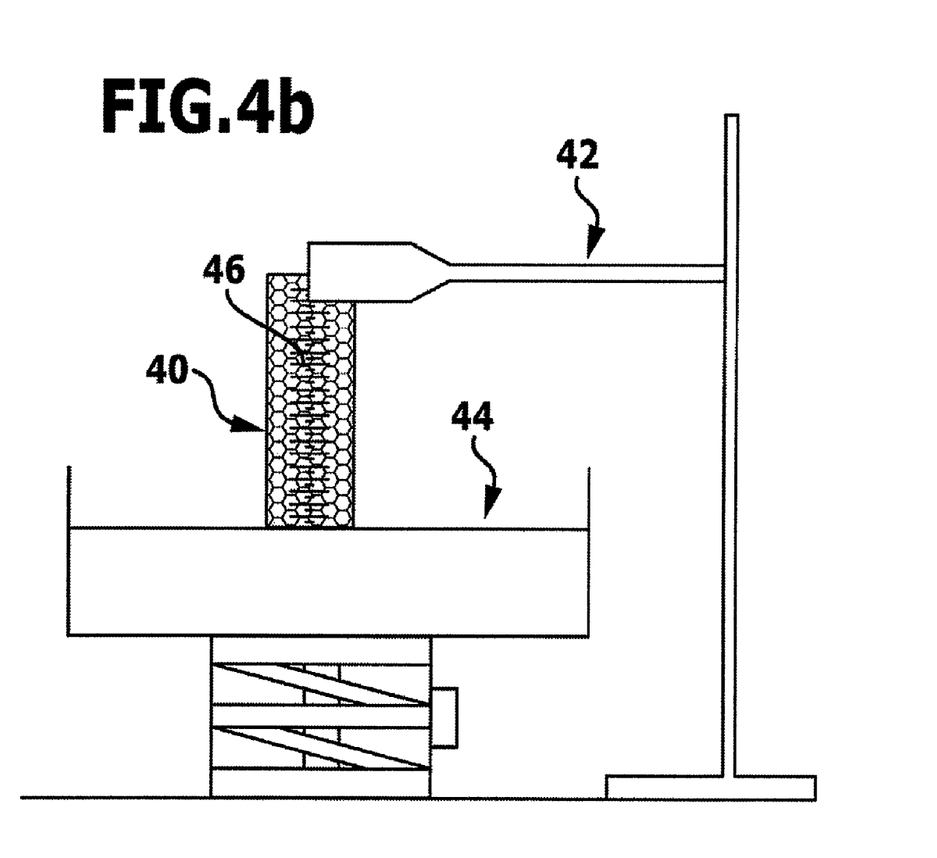
Figure 4C:
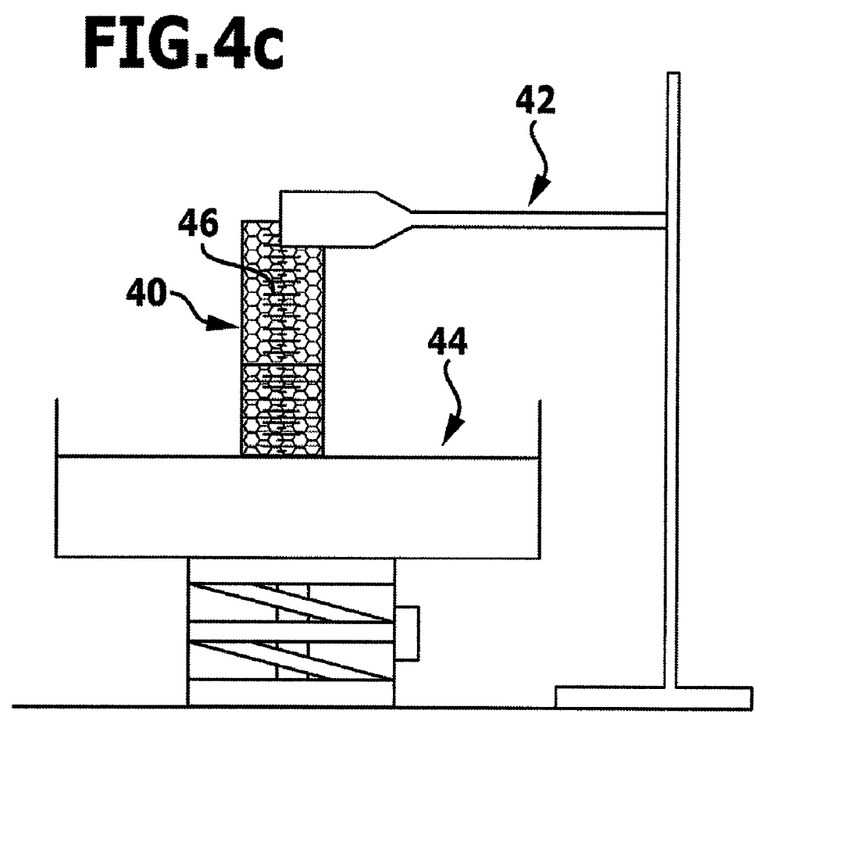

In FIGS. 4a to c, the principle for measuring the height of rise per unit of time is illustrated schematically. The prepared sample 40 is clamped via a holding device 42 so as to hang freely downwards and placed over a basin 44 with temperature-controlled water (25° C.). At the beginning of the measurement, the basin with the water is moved upwards to such an extent that the sample dips into the supply of water to a depth of 2 mm. Subsequently, the height of rise which is generated via capillary forces is registered as a function of time and then entered in the graph according to FIG. 3. A measuring stick 46 applied to the sample 40 makes the reading of the height of rise easier.

Figure 5A:
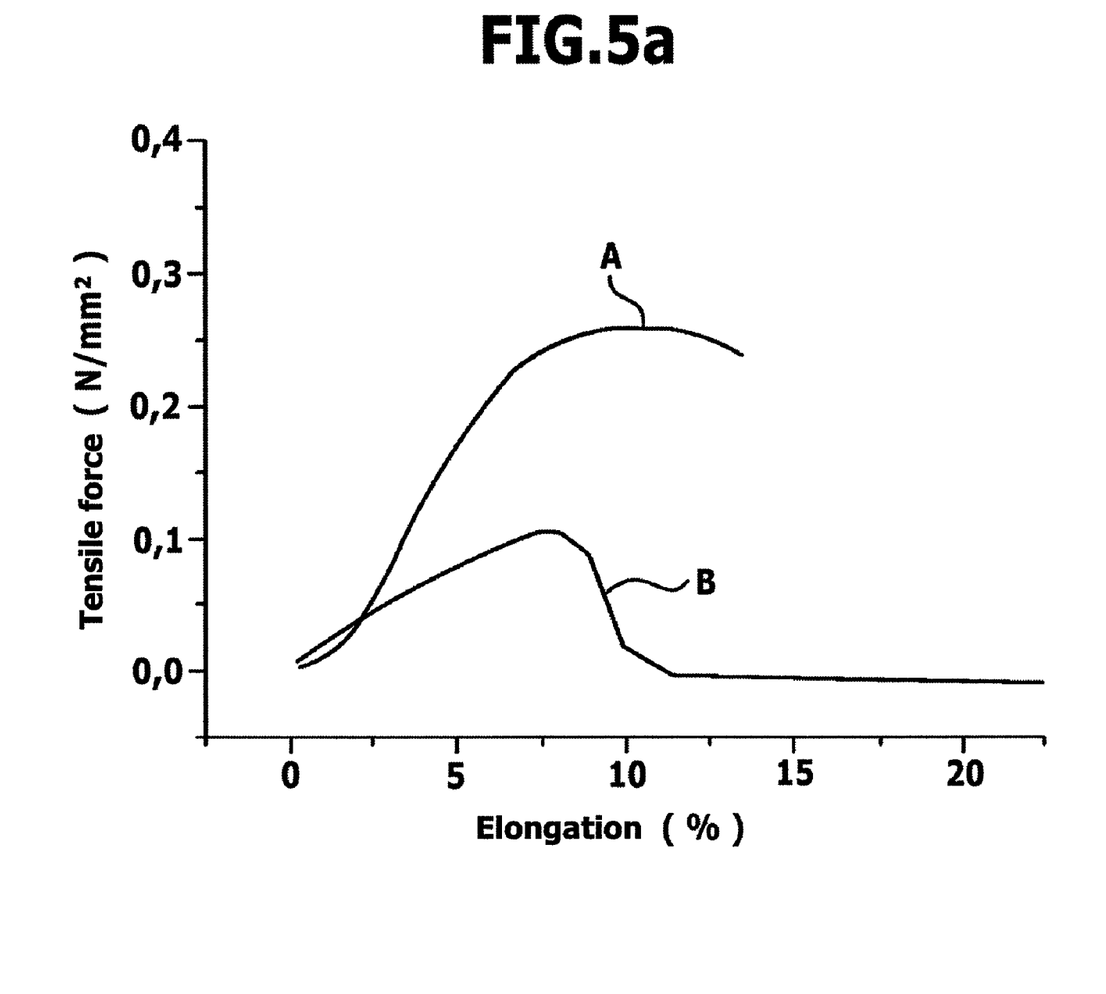
FIGS. 5a and b show tension/elongation results for conventional cell carrier materials and those according to the invention.

Tension/elongation measurements were also carried out on the samples described above with a width of 15 mm and a thickness of approximately 1 mm, namely in the dry state (FIG. 5a). Only the two samples based on gelatin were compared, i.e., on the one hand, the fleece produced in accordance with the invention and, on the other hand, the conventional sponge sample with the same dimensions.

It is apparent from FIG. 5a that the gelatin fleece in accordance with the present invention has a considerably higher specific tensile strength in comparison with the gelatin sponge in the dry state (water content approximately 10% by weight) and, in addition, allows a considerably greater elongation in the dry state, as well. Whereas the tension/elongation curve for the gelatin sponge sample (curve B) already breaks off after an elongation of approximately 7 to 8%, i.e., the sample tears, the fleece sample according to the invention may be stretched by approximately 17% before any tearing of the sample is observed. In this respect, a considerably higher tensile strength in comparison with the sponge sample is also ascertained.

In the completely hydrated state of the samples (FIG. 5b), i.e., in a state, in which the cross-linked gelatin material of the sponge or of the fleece according to the invention are completely swollen, even greater and more significant differences are obtained. The water content is, in this case, more than 100% by weight in relation to the gelatin material.

Figure 5B:
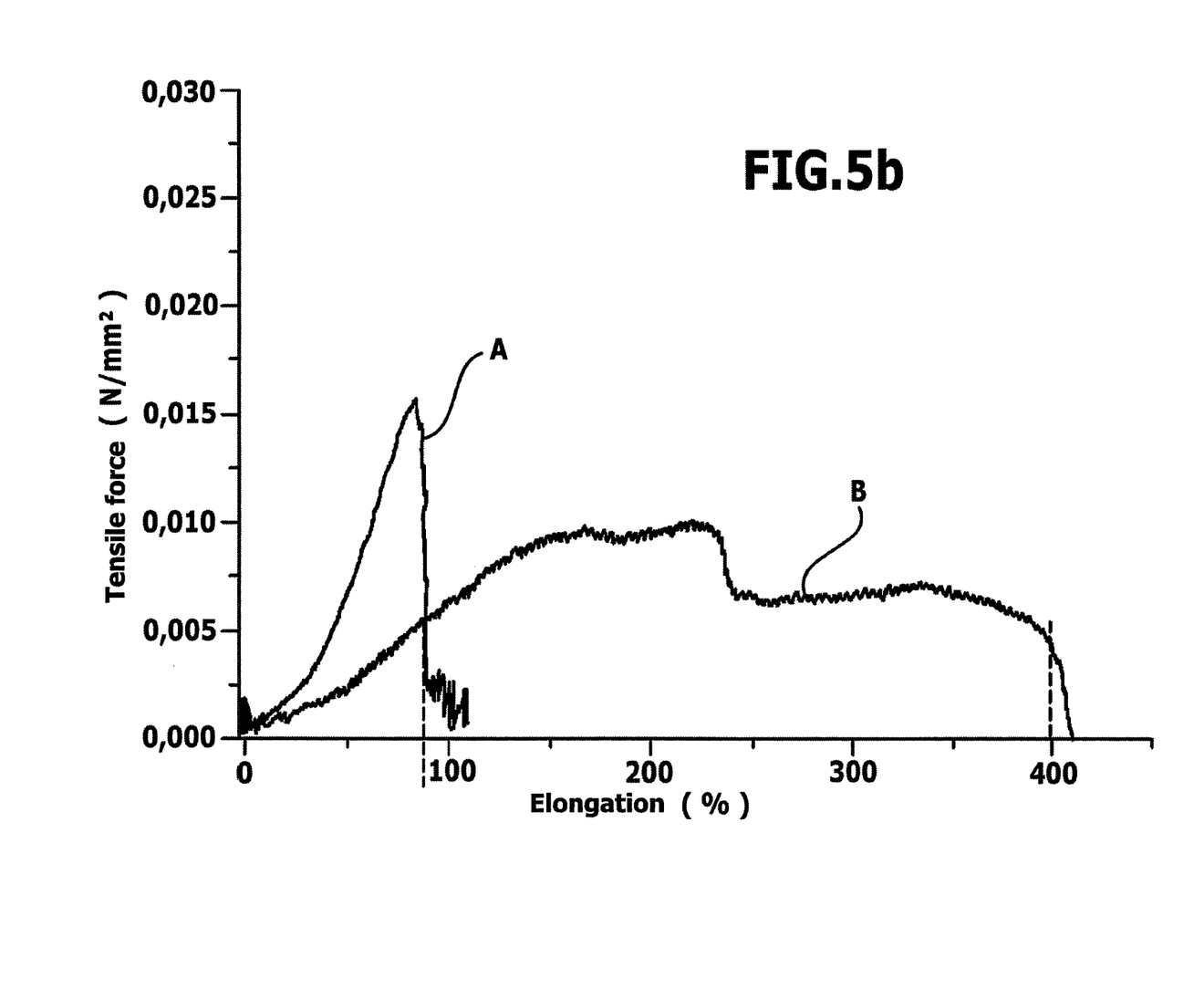

A standard sponge in the size 80×50×10 mm as well as the fleece according to the invention in the size 80×50×1 mm were used for the comparison. The sponge has a dry weight per unit area of 120 g/m², the fleece one of 180 g/m².

In this case, tearing of the sample is observed for the sponge sample after an elongation of just about 75% (curve B) whereas the fleece sample according to the invention may be stretched to 400% (curve A) before it finally tears. In the hydrated state, as well, the fleece (with 2.6 N tensile force) achieves a higher strength than the sponge.

This is of quite particular significance for the use of the fleece materials as carriers for cell implants since this gives the attending physician the possibility of deforming, stretching and adapting the cell implant to the conditions of the wound of the patient to be treated almost as required.

Example 3

Production of Sugar-Free Candy Floss

Analogous to Example 1, a 20% by weight aqueous spinning solution is produced with the following composition:
15 g of gelatin type A, 260 Bloom, edible quality
15 g of gelatin hydrolysate type A, average molecular weight 3 kD
70 g of water Coloring matter (e.g., raspberry) and aromas (e.g., vanilla-cola) can be added according to the producer's specifications.

The spinning solution is heated to 70° C. and spun in the spinning rotor.

The product collected has the consistency and sensory perception of candy floss.

The invention claimed is:

1. A non-woven fiber fabric, comprising fibers consisting of a gelatin material, the fibers having a thickness on average of 1 to 500 μm, wherein the non-woven fiber fabric has a plurality of areas where two or more fibers merge into one another without any phase boundary, and wherein the non-woven fiber fabric contains two or more fiber fractions consisting of the gelatin material with different average fiber thicknesses of 1 to 500 μm.

2. The non-woven fiber fabric as defined in claim 1, wherein the gelatin material of the fibers is amorphous to 60% by weight or more.

3. The non-woven fiber fabric as defined in claim 1, wherein the tear resistance is 0.15 N/mm² at a specific weight per unit area of the non-woven fiber fabric of 140 to 180 g per m² in a dry state and the breaking elongation of the non-woven fiber fabric in a hydrated state is 150%.

4. The non-woven fiber fabric as defined in claim 1, wherein the non-woven fiber fabric contains at least one additional type of fiber comprising an additional material different from the gelatin material.

5. The non-woven fiber fabric as defined in claim 4, wherein the additional material is selected from chitosan, carrageenan, alginate, pectin, starch and starch derivatives, regenerated cellulose, oxidized cellulose and cellulose derivatives, gelatin derivatives and gelatin copolymers.

6. A flat material with one or more layers, wherein at least one of the layers contains a non-woven fiber fabric as defined in claim 1.

7. The flat material as defined in claim 6, wherein a first layer contains a non-woven fiber fabric of fibers with a first average fiber thickness and a second layer contains a non-woven fiber fabric of fibers with a second average fiber thickness, wherein the second average fiber thickness is greater than the first average fiber thickness.

8. The flat material as defined in claim 6, further comprising a membrane extending parallel to the non-woven fiber fabric.

9. The flat material as defined in claim 6, wherein the non-woven fiber fabric is colonized by living cells.

10. A preliminary product for foods comprising the non-woven fiber fabric as defined in claim 1.

11. A material for the production of a depot medicine comprising the flat material as defined in claim 6.

12. A carrier for a pharmaceutical substance comprising the non-woven fiber fabric as defined in claim 1 and a pharmaceutical substance.

13. The carrier as defined in claim 12, wherein the pharmaceutical substance contains thrombin.

14. The carrier as defined in claim 12, wherein the pharmaceutical substance contains cell growth modulators.

15. A method for producing the non-woven fiber fabric as defined in claim 1, comprising
   (a) providing an aqueous spinning solution containing a gelatin material;
   (b) heating the spinning solution to a spinning temperature; and
   (c) processing the heated spinning solution in a spinning device with a spinning rotor.

16. The method as defined in claim 15, wherein the aqueous spinning solution contains a proportion of gelatin in the range of approximately 10 to approximately 40% by weight.

17. The method as defined in claim 15, wherein processing the heated spinning solution in a spinning device comprises using a spinning rotor, the rotor having spinning openings of different sizes so that fibers with different average thicknesses result.

* * * * *

UNITED STATES PATENT AND TRADEMARK OFFICE
CERTIFICATE OF CORRECTION

| | | |
|---|---|---|
| PATENT NO. | : 8,226,970 B2 | Page 1 of 1 |
| APPLICATION NO. | : 12/549629 | |
| DATED | : July 24, 2012 | |
| INVENTOR(S) | : Michael Ahlers et al. | |

It is certified that error appears in the above-identified patent and that said Letters Patent is hereby corrected as shown below:

On the Title Page:

At Item (73) please add the following Assignee:

Carl Freudenberg KG, Weinheim (DE)

Signed and Sealed this
First Day of January, 2013

David J. Kappos
*Director of the United States Patent and Trademark Office*